United States Patent [19]

Steinemann

[11] Patent Number: 4,945,342
[45] Date of Patent: Jul. 31, 1990

[54] ELECTRICAL CABLE FOR PERFORMING STIMULATIONS AND/OR MEASUREMENTS INSIDE A HUMAN OR ANIMAL BODY AND METHOD OF MANUFACTURING THE CABLE

[75] Inventor: Samuel G. Steinemann, St. Sulpice, Switzerland

[73] Assignee: Instit Straumann, Switzerland

[21] Appl. No.: 254,367

[22] Filed: Oct. 5, 1988

[30] Foreign Application Priority Data

Oct. 16, 1987 [CH] Switzerland .......................... 4082/87

[51] Int. Cl.⁵ .............................................. H01B 5/68
[52] U.S. Cl. ............................ 174/113 R; 174/113 AS;
174/119 R; 174/117 AS; 128/784
[58] Field of Search ........ 174/113 R, 113 AS, 119 R,
174/117 AS; 128/419 D, 784, 785, 786

[56] References Cited

U.S. PATENT DOCUMENTS

| | | | |
|---|---|---|---|
| 2,268,223 | 12/1941 | Peterson | 174/113 R |
| 3,333,045 | 7/1967 | Fisher et al. | 174/130 |
| 3,760,812 | 9/1973 | Timm et al. | 174/130 X |
| 4,033,357 | 7/1977 | Helland et al. | 128/785 |
| 4,198,991 | 4/1980 | Harris | 128/784 |
| 4,514,589 | 4/1985 | Aldinger et al. | 128/784 X |
| 4,524,241 | 6/1985 | Binder et al. | 174/119 R |
| 4,566,467 | 1/1986 | DeHaan | 128/784 |
| 4,640,983 | 2/1987 | Comte | 174/119 R |
| 4,677,989 | 7/1987 | Robblee | 128/784 |

FOREIGN PATENT DOCUMENTS

| | | | |
|---|---|---|---|
| 524346 | 12/1953 | Belgium | 174/113 AS |
| 0162178 | 11/1985 | European Pat. Off. | |
| 2241932 | 3/1973 | Fed. Rep. of Germany | 174/117 AS |
| 2505928 | 8/1976 | Fed. Rep. of Germany | |
| 1571849 | 6/1969 | France | |
| 204765 | 9/1987 | Japan | 128/784 |
| 1219017 | 1/1971 | United Kingdom | 128/784 |

OTHER PUBLICATIONS

"Requirements of the Ideal Pacemaker Lead", A. Sinnaeve et al., pp. 47–55, (Elsevier Science Publications, B.V., Amsterdam, 1985).

Primary Examiner—Morris H. Nimmo

[57] ABSTRACT

The cable comprises one or more fiber bundles having 100 or more fibers per bundle, the diameter of the fibers having a value smaller than 20 micrometers, and the fibers preferably consisting of an alloy containing titanium as base metal and, in addition, at least one metal from the group including niobium, tantalum, zirconium, chromium, molybdenum, iron and aluminum. The bundle may be wound around the longitudinal axis of the cable and/or plaited with other bundles. Furthermore, the fibers of a bundle may be twisted (snaked), circumstances permitting. Each bundle and its fibers should, however, run to advantage in a way to have the length of the bundle as well as the length of each fiber of the bundle preferably be not more than 50% and, for example, not more than 30% longer than the cable. The fibers may be bent down to very small radii of curvature, without any fatigue failures taking place, while a relatively low electrical resistance of the cable may be achieved. The fibers are covered on their outer surfaces by a metal oxide layer, effective to insulate the fibers, in addition to the normally provided rubber-elastic insulation.

37 Claims, 2 Drawing Sheets

ELECTRICAL CABLE FOR PERFORMING STIMULATIONS AND/OR MEASUREMENTS INSIDE A HUMAN OR ANIMAL BODY AND METHOD OF MANUFACTURING THE CABLE

BACKGROUND OF THE INVENTION

1. Field of the Invention

The present invention refers to an electrical cable for performing stimulations and/or measurements inside a human or animal body to be used in conjunction with electrical or electronic instruments, such as a cardiac pacemaker. The cable may comprise one or more bundles of electrically conducting wires. It should be understood, therefore, that whenever the term bundles is referred to in plural, the singular is meant to be included, unless the formation under discussion clearly includes several bundles, as for example a plaited, woven or twisted formation. The invention equally refers to a method for manufacturing the cable of the invention.

2. Description of the Prior Art

Cables of this type are commonly used in medicine and surgery in conjunction with electrical and/or electronic equipment, and are implanted together with such equipment into a human or animal body for the purpose of stimulation, measurement and recording of physiological variables, and thus for research, therapy and the management of patients with cardiological, neurological and other diseases. The cardiac pacemaker is a classical example of such equipment.

In an article titled "Requirements of the Ideal Pacemaker Lead" by A. Sinnaeve, R. Willems and R. Stroobandt, appeared in the publication "Pacemaker Leads" (pages 47–55), edited by A.E. Aubert and H. Ector (Elsevier Science Publications B.V., Amsterdam, 1985), the authors elaborate in detail on the requirements of pacemaker leads. Such leads (referred to as cables in the present specification) are subject to repetitive mechanical stresses, by being moved and deformed in the course of every heartbeat, adding up to approximately 37 million of repetitions each year. To these are added the stresses due to the movements of breathing, the movements of the arms, and the other bodily movements. There result in the lead bending stresses and deformations, primarily, but also torsional stresses and deformations, as well as tension stresses and elongations. The leads or cables are required to stand up to these mechanical loads without breaking, they should have a preferably low electrical resistance. They should also have a high corrosion resistance in regard to blood and other bodily fluids, and be as thin as possible.

Many of the known pacemaker leads comprise wires of circular or rectangular cross-section. The wires frequently consist of a platinum-iridium alloy, of alloys containing silver or gold, of the alloys commercially available under the names Elgiloy and MP35N and comprising cobalt, chromium, nickel and other components, or of tungsten, stainless steel and aluminium or copper. The cables are commonly provided with insulation on the outside and sometimes they comprise a core made of insulating material. In this connection reference is made to the article by Sinnaeve et al. cited above, as well as to US-PS 4,640,983. In most of the known cables, having wires of circular cross-section, the diameters of these wires are in the order of magnitude of about 0.1 mm or more. In US-PS 4,640,983 are recommended diameters of 20 to 80 micrometers for wires of circular cross-section, whereas the wires actually used are specified as 50 micrometers in diameter.

In most of the known cables the wires are wound individually. In the cited US-PS 4,640,983 the wires are wound in bundles, to helices, the helical pitch of the wires, or the wire bundles, being generally made rather small, resulting in adjacent helical windings abutting against each other, or pretty nearly so. To be sure, the wire or fiber pliability (flexibility) may be improved in this way, as compared to wires disposed in straight line. However, when the wires are bent to small radii of curvatures, fatigue fractures may occur, this being also a function of the type of wire used. If, due to such a fracture, current interruption takes place in the cable of a cardiac pacemaker, the patient may be instantly killed. Such fractures are therefore dangerous possibilities.

In US-PS 4,640,983, the cable is wound into helices consisting of bundles, each comprising seven twisted wires. These cables are said to show fatigue resistance down to values of bending radii as low as 1.5 mm. However, the task of shaping bundles of intertwisted wires into coils to follow the form of multiple threads is rather difficult and elaborate.

In all known cables having wires wound to coils and their winding substantially abutting against one another, the wound-off length of the wires is made to be a multiple of the length of the corresponding cable. This results in the disadvantage, that the electrical resistance is largely increased. To compensate for this disadvantage the wires, or at least some of them may be made of a material having a low specific electrical resistance, such as platinum-iridium, silver, or copper. To be sure these materials have unfavourable mechanical properties. Platinium and iridium as well as silver are relatively expensive, whereas copper may become toxic, when brought in contact with bodily fluids or cells.

If a cable of wires and plastic insulation surrounding the wires is implanted into a human or animal body the possibility may arise that the insulation will suffer damage when during cable insertion, or later on during any movements of the bodily parts that accommodate the cable. The result may be that the electrical energy supplied will get short-circuited into the human or animal body before reaching the end of the cable. This could happen with all of the wire materials specified before except perhaps with aluminium. For the sake of clarification let some additional geometrical and physical variables and their mutual relationships be now explained. In the following, the term critical radius of curvature $r_c$ will be used to refer to the smallest radius of curvature to which a cable wire or fiber may be bent, without causing any fracture. If a wire or a fiber of a cross-sectional moment of inertia I, and a section modulus W, and of a material having a modulus of elasticity E and a maximum allowable tensile stress $\sigma_z$, then the critical radius of curvature may be expressed by the formula:

$$r_c = \frac{EI}{W\sigma_z} \quad (1)$$

If the wire or fiber has a circular cross-section and a diameter d, then $$W = \frac{2I}{d},$$

and the critical radius of curvature becomes:

$$r_c = \frac{Ed}{2\sigma_z} \quad (2)$$

The electrical resistance R of a conductor of a material with specific electrical resistance $\rho$, length 1, and cross-sectional area A, may be expressed as:

$$R = \frac{\rho l}{A} \quad (3)$$

The formula (2) implies that the critical radius of curvature is proportional to the modulus of elasticity, and inversely proportional to the allowable tension stress, and proportional to the diameter d for wires or fibers of circular cross-section. One alloy frequently used in conjunction with known cables is the platinum-iridium alloy, which consists of 10% by weight iridium and the rest platinum. This alloy has a comparatively high modulus of elasticity, specifically about 150 GPa, and a comparatively low allowable tension stress, specifically 0.3 GPa. If the wires are assumed to have a circular cross-section of a diameter of 0.1 mm, then, by inserting the above values into formula (2) there results a critical radius of curvature of 25 mm. However, the curvatures actually occurring when implanting a cable into the body, will be considerably smaller and thus below critical. This can be partially compensated by high-strength cobalt-alloys also used for making cables. These alloys have higher allowable tension stresses, to be sure, but even higher moduli of elasticity than the previously mentioned platinum-iridium alloy. Furthermore, it is difficult to form them to thin wires.

It is known in the field of superconductivity to inbed into a copper matrix a relatively large number of relatively thick wires of a titanium-niobium alloy, and to stretch the resulting composite conductor to thus make it thinner. There results a composite conductor containing titanium-niobium wires imbedded into a copper matrix and having diameters between 12 and 13 micrometers. Such a composite conductor cannot be used, however, as implant into a human or animal body. It is unsuited for such a purpose, because its outer diameter is of the order of magnitude of 1 mm, making the conductor very rigid, and also because copper may turn out to be toxic inside the body, as previously mentioned.

SUMMARY OF THE INVENTION

Hence from what has been explained heretofore it should be apparent that the art is still in need of an electrical cable for performing stimulations and/or measurements inside a human or animal body, a cable not associated with the aforementioned drawbacks and limitations of the state-of-the-art proposals.

It is therefore a primary object of the present invention to provide a novel electrical cable for performing stimulations and/or measurements inside a human body which is not associated with the drawbacks and limitations of the prior art as heretofore discussed and which effectively and reliably fulfills an existing need in the art.

Another and more specific object of the invention relates to a new and improved electrical cable for performing stimulations and/or measurements inside a human or animal body in conjunction with electrical and/or electronic equipment, such as a cardiac pacemaker, in which cable the danger of fatigue fractures, electrical leakages and the possibility of toxic effects inside the body should be largely eliminated, while a low electrical resistance of the cable and an economical method of manufacturing the cable should be made possible.

The foregoing and other objects are attained in accordance with one aspect of the invention by providing an electrical cable for performing stimulations and/or measurements inside a human or animal body, to be used in conjunction with electrical and/or electronic instruments, such as a cardiac pacemaker, the cable comprising one or more bundle of wires. According to the invention the wires are implemented as fibers less than 20 micrometers thick.

The invention also concerns a method of manufacturing an electrical cable of the aforementioned kind, wherein a number of relatively thick wires of the same material as the fibers to be made are imbedded into a matrix consisting of a different material and are subjected, together with the matrix, to a deformation process in the course of which the wires are made longer, and thinner, wherein, furthermore the matrix is subsequently dissolved by an acid to thus yield one or more bundles of fibers.

The cable is adapted to be implanted partially or completely inside a human or animal body and to become part of a device for stimulation and/or measurement. The cable may be adapted for stimulating the heart, by way of a cardiac pacemaker. Stimulation of nerves and/or muscles are also possibilities. Furthermore, the cable may be adapted to carry electrical signals generated by body cells to a measuring device. Also the cable may be adapted to carry electrical current from a current source, to an activating device located inside a bodily part, or from a sensor located inside a bodily part, to a measuring device.

The fibers are preferably made circular in cross-section, not considering irregularities due to surface roughness, but could possibly have a different, roundly cross-sectional shape, deviating more or less from a circle. In this latter case, the "thickness" of the fibers is meant to refer to their maximum cross-sectional dimension.

The invention is rooted in the recognition, that when implanting a cable to be connected to a cardiac pacemaker or to another similar device, the cable could become subjected to bends of radii of curvature as low as 1 to 2 mm. However, the diameter of the thinnest manufacturable cable used in the art lies within the same range of 1 to 2 mm. By using fibers according to the invention of less than 20 micrometers, and preferably less or equal to 15 micrometers maximum, the critical radius of curvature becomes lowered to less than 2 mm, for example to less than 1.5 mm, or even less than 1 mm. The feasible corresponding fiber thickness may be less than 5 micrometers or more.

The cable may comprise one single bundle of fibers, or preferably two or more fiber bundles. Each bundle may contain 100 or more, 200 or more, 500 or more, 1000 or more and even up to 3000 fibers, in dependence of the number of available bundles and of the desired value of electrical conductance, i.e. the reciprocal value of the electrical resistance.

The fibers belonging to a bundle may run parallel to the longitudinal axis of the bundle, or they may be wound around the latter axis. Such fibers should be preferably held together with such looseness, that adjacent fibers be able to perform limited movement relative to each other. However, they should also preferably rest against each other, at least in places, and exert a certain minimum compression force, sufficiently large however, to enable electrical contact between adjacent fibers to take place, at least in places, in spite of any oxide layers covering the fibers, a feature to be yet explained in more detail.

Each bundle of fibers belonging to a cable may form an angle with the longitudinal direction of the cable, at least at most of its sections, and be specifically zigzag-shaped and/or wave-shaped and/or helix-shaped. The cable may comprise bundles of fibers, loosely arranged or loosely held together for example by being plaited, knit, woven or twisted, resulting in interspaces between adjacent bundles, at least in places. The bundles will then be able to move to a limited extent, relative to each other. As a result, a fiber configuration including the totality of fibers may show good deformability and the possibility to stretch the fiber configuration beyond the extensibility of the individual fiber, as well as the possibility of bending and torsional deformations and a certain elasticity of form. Whereas the elastic extensibility of the individual metallic fiber typically lies in the order of 1%, it is possible to make the aforementioned fiber configuration to be stretched by as much as 10% or even 20%, depending upon requirements and to impart it a low bending and torsional stiffness. For applications not requiring particularly large values of cable extensibility, the fiber bundles of a cable may be arranged to run parallel to the longitudinal axis of the cable.

Normally, it is of advantage to have the fibers run at least substantially obliquely to the longitudinal direction of the cable to endow the cable with good deformability, good flexibility and good twistability. This may be achieved, as described before, by twisting the fibers around the longitudinal axis of their bundle and/or by arranging the bundle or each bundle, respectively to make it run at least substantially obliquely to the longitudinal direction of the cable.

If the individual fibers are wound around the longitudinal axis of their bundle, the so-formed coils should be stretched to a large extent. The term stretched is used here to mean, that the fibers should have pitches large enough to have the wound-off length of each fiber be only slightly larger than the length of the bundle associated with said fiber, specifically, by less than 20%, preferably by less than 10%, and for example by less than 5%. If the bundle follows a zigzag-, wave or helix-shape, then the zigzag-, wave- or helix-shaped line described by the bundle should also be greatly stretched, so that the woundoff length of the bundle, as well as the wound-off lengths of the individual fibers be only slightly larger than the length of the entire cable. The length of each bundle, and also the length of each of its fibers should be larger than the length of the cable itself, preferably by 50% or less, or for example by 30% or less. If a cable comprises for example a helix generated by a single bundle, or by several bundles in the manner of a multiple thread, there should be open clearance spaces provided between neighbouring bundle windings, to be preferably considerably larger than the bundle thickness, and to amount for example to a multiple of the bundle thickness. The ratio between the length of a fiber bundle, or the length of an individual fiber, and the length of the cable is equal to the reciprocal value of the cosinus of the angle that the bundle, or the fiber, forms with the longitudinal direction of the cable. If this angle varies along the cable, then this ratio is specified as a weighted average value of the angle. The specified limiting values applying to the differences in length between the fibers, bundles and cables, may be implemented by making the angle formed by the fiber bundles and their fibers, with the longitudinal direction of the cable, to amount to not more than about 30° or even not more than about 20° If the fibers are made not more than 50% longer, or by not more than 30% longer than the cable, then the possibility exists to obtain an electrical resistance of a fiber that is only larger by a corresponding percentage than the resistance of a fiber running parallel to the longitudinal direction of the cable. A pattern of the kind not running parallel to the direction of the cable and/or fiber bundles will then yield a considerably smaller increase in resistance than the helix shape of the wires used in many of the known cables, in which neighbouring helical windings substantially abut against each other and the length of a wire has the value of a multiple of the length of the cable. Since the cable according to the invention may be arranged to have the fiber bundle and its fibers form comparatively small angles at most, with the longitudinal direction of the cable, without any loss in flexibility, it is also possible to achieve, by means of a cable according to the invention, a relatively small electrical resistance, if the specific electrical resistance of the fiber material is not particularly low and/or if the total cross-sectional area of the fibers is comparatively small.

The fibers comprise a metallic material containing at least one metal. In a preferred embodiment the fibers consist of an alloy containing one or more of the metals niobium, tantalum, zirconium, chromium, molybdenum, iron and aluminium, in addition to the base metal consisting of titanium. The proportion of titanium in the alloy in percent by weight should be the largest and, in general, should be not less than 50 percent. Furthermore, not considering any impurities present, the fibers should preferably not contain any other metals but titanium and the previously mentioned alloy components. The alloy of which the fibers are to be make should preferably be cold-formed, which it to mean that at least the terminal part or terminal phase of the process of deformation in which the fibers are produced, is a cold forming process. This process is yet to be explained in detail.

The cable is preferably provided, on the outside, at least, with electrical insulation consisting of a rubber-elastic, pliable and bio-compatible material, for example of an elastomer based on polyurethane or silicon. If used in conjunction with a cardiac pacemaker, and for other purposes too, it is of advantage to make the cable hose-shaped and provided with a longitudinal hollow space open at one end and closed at the other end, in which space a so-called stylet may be transiently inserted. The fibers of a cable may constitute, together, a single conductor, or they may be subdivided into groups insulated against each other, each such group to form an individual electrical conductor.

Titanium and the titanium alloys made reference to before also possess good strength and a relatively low modulus of elasticity, this latter feature being of particular advantage, because it keeps bending stresses low. Titanium belongs to the group of metals of the alpha-type. Depending on their composition, titanium alloys may have varying phase structures, and may correspondingly belong to the alpha-, the alpha-beta- or the beta-type. The TiNbTaAl alloy containing 3% by weight niobium, 1% by weight tantalum, 6% by weight aluminum and the rest titanium, belongs for example to the alpha-type. The group of alloys of the alpha-beta-type includes for example the alloy TiAlFe containing 5% by weight aluminum, 2.5% by weight iron and the rest titanium, as well as the alloy TiNbAl containing 7% by weight niobium, 6% by weight aluminum and the rest titanium. The group of alloys of the beta-type includes the alloy TiNb containing 40% by weight niobium and the rest titanium, as well as the alloy TiMoZrAl containing 15% by weight molybdenum, 5% by weight zirconium, 3% by weight aluminum and the rest titanium. The modulus of elasticity typically lies at 100 to 120 GPa for the alloys of the alpha-type and alpha-beta-type and at about 65 to 110 GPa for the alloys of the betatype, the exact values depending upon the heat treatment applied. The alloys of the beta-type have a cubic structure and, as a feature shared to some extent by the alloys of the alpha-beta-type they display larger plastic deformability than titanium and than the alloys of the alpha-type having a hexagonal structure. Thus, the alloys of the alpha-beta-type and, above all, the alloys of the beta-type have more advantageous features than the materials of the alpha-type. Also the mechanical strength of the alloys of the beta-type may be increased by heat treatment, such as solution-annealing and/or aging.

The cold-formed TiNb-alloy of the beta-type referred to before has a modulus of elasticity of about 69 or 70 GPa. The ultimate tension or fracture stress, upon single application of a tension load, has a value of 0.88 GPa, whereas the fatigue stress, i.e. the stress allowable while applying bending loads repeated any number of times, has a value of 0.4 GPa. If the formula (2) is resolved for the fiber diameter d, and if the value of the modulus of elasticity is inserted for E and the value of fatigue stress is inserted for $\sigma_z$, or more accurately, instead of $\sigma_z$, both of these values to refer to TiNb, and if a critical radius of curvature of 1.5 mm is assumed, there results a fiber diameter d of 17 micrometers.

If the previously mentioned PtIr-alloy used for known cables and having E=150GPa and a fatigue stress of 0.3 GPa were to be employed for achieving a critical radius of curvature of 1.5 mm, then the fiber diameter would have to be about 6 micrometers and thus considerably thinner than the diameter required in case of a TiNb-alloy. If using a high-strength cobalt alloy having E=230 GPa and a fatigue stress of 0.8 GPa, the fiber diameter would have to be 10 micrometers. To be sure, the platinum-iridium alloys, and more so the cobalt alloys, have considerably worse plastic deformation properties than titanium and the titanium alloys, so that making sufficiently pliable fibers of platinum-iridium alloys and of cobalt-alloys would be comparatively difficult.

The bending stiffness S of an individual fiber may be expressed as the product EI, in which E and I have the meanings specified in conjunction with the formula (1). The bending stiffness of a bundle of loosely held together parallel or perhaps slightly twisted fibers is substantially equal to the product of the number of fibers times the bending stiffness of an individual fiber. The bending stiffness of a bundle of fibers is considerably smaller than that of an individual wire having a cross-section equal to the total cross-sectional area of the fibers of a fiber bundle. A bundle having 200 fibers consisting of the aforementioned TiNb-alloy and having a diameter of 17 micrometers, possesses, for example, a bending stiffness of $5.7 \times 10^{-8} Nm^2$. An individual wire made of the same material and having a cross-sectional area equal to that of 200 fibers would have a diameter of 240 micrometers as well as a bending stiffness 200 times larger and equal to $1.1 \times 10^{-5} Nm^2$.

The specific electrical resistance of titanium has a value of $42 \mu\Omega cm$, whereas that of titanium alloys a value of $90 \mu\Omega cm$. For the purpose of comparison let it be pointed out, that the specific resistance of the PtIr-alloy used in known cables and containing 10% by weight iridium and the rest platinum is $25 \mu\Omega cm$, whereas the specific resistance of the cobalt-alloys also used in known cables lies around $70 \mu\Omega cm$. To be sure, titanium and its alloys have a larger specific resistance than the PtIr-alloy; this, however, may be compensated for in the cables of the invention by the fact, that fibers, as noted before, must only be slightly longer than the cable, whereas in the known cables the length of the wires is normally a multiple of the length of the cable.

Titanium is reactive toward oxygen. As a matter of fact, if a fiber consisting of titanium-alloy is placed into an environment containing free or bound oxygen effective to act in an oxidizing manner and is subjected to the action of atmospheric oxygen or of electrolytic liquids, then a compact film-like metal oxide layer, specifically $TiO_2$ in the case of titanium, will get generated on the outer surface of the fiber. In similar fashion, the metals previously mentioned as possible alloy components, specifically, niobium, tantalum, zirconium, chromium and aluminum, are reactive toward oxygen Also iron, if a component of a titanium alloy, will be similarly covered by a layer of oxide.

The layer of oxide generated on the outer surface of each fiber by spontaneous oxidation typically possesses a thickness in the order of magnitude of 3 nm. If thicker layers of oxide are desired, such thicknesses may be increased up to about 50 nm or more by anodic oxidation.

The layers of oxide generated spontaneously and/or increased in thickness by anodic oxidation, as the case may be, are effective to protect the metal against corrosion. Therefore, if the cable insulation normally provided suffers damage, and some fibers will come in contact with blood or other bodily fluids or with bodily cells, practically no corrosion will take place. Furthermore, titanium and its alloys are free of toxicity and display biologically inert behaviour.

A layer of oxide generated spontaneously on the outer surface of a fiber and/or increased in thickness by anodic oxidation, is effective to act as an electrical insulator, provided that no significant compression forces act upon it, the insulating effect being dependent upon the polarity of the voltage. In the case of anodic polarization, i.e. if a positive voltage acts on the metal, then the layer of oxide will be insulated up to a breakdown voltage dependent upon the specific metal, but having a value of at least 3 volts. If the voltage is of reversed polarity, then, up to 10 volts or more, there will flow through the layer of oxide but negligibly small current. If, however, wires of titanium or of titanium alloy, of an insulated cable, will come in contact with bodily fluids or bodily tissue, due to damaged insulation, then the layer of oxide will prevent any undesirable electrically conducting connection with the body at the place of damaged insulation, provided that no compression forces act upon the oxide layer. However, if compression forces do act upon the fibers and upon their oxide layers, then these layers will lose their electrically insulating effect. It is therefore possible that if adjacent fibers are made to come into mutual contact, in places, under the action of a certain minimum compression force, then electrically conducting spots may arise at the places of contact, in spite of the presence of the layer of oxide. If, therefore, one fiber in a bundle should break, then some of the adjacent fibers may be able to electrically bridge over the fractured location, with the result that the fracture will not result in any significant increase of the electrical resistance. Evidently, the fibers of one or several bundles at the ends of a cable may be readily electrically connected with any other electrically conducting body, such as a contact electrode or a connector of an electronic pulse generator.

As noted before, the cables are generally provided with a rubber-elastic electrical insulation. Since the layers of oxide generated on the surfaces of the titanium or the named titanium-alloy fibers are effective to protect these against corrosion and to act as electrical insulation, the rubber-elastic insulation may be dimensioned comparatively thin. Thus small cross-sectional dimensions, i.e. small diameters and small cable stiffness values may be achieved.

Metallic fibers having diameters less than 20 micrometers cannot be made using the methods commonly employed for manufacturing individual wires. Such fibers may however be made as bundles, starting out with comparatively thick wires of preferably circular cross-section and consisting of the material of the fibers to be formed, in a number corresponding to the desired number of fibers in a bundle. These thick wires are inserted into bores of a block that consist of a metallic material different from the material of the fibers. The block, functioning as a matrix, should be of a material preferably softer than the material of the fibers and have similar ductility properties as this material, in regards to deformations of elongation. A suitable material for the matrix may be for example copper or a copper-nickel-alloy. The composite blank now consisting of the matrix and the wires imbedded into the matrix may be stretched and reduced in diameter, in steps, by hot and/or cold pressing and/or rolling and/or drawing. As a result, the wire thickness will shrink to the desired fiber thickness. The terminal step or phase of the deformation process, at least, is to preferably be a cold forming process. Such deformation may be performed by warm pressing and subsequent cold drawing. In a deformation process of this kind, the volume of the blank, as well as that of the individual wires will remain constant. As noted before, a similar method of deformation is used in the art for making superconductors, the fibers involved consisting of a titanium-niobium-alloy imbedded into a copper matrix. To be sure, when making the superconductors, the matrix remains preserved, whereas in the present method of manufacturing fibers for an electrical cable, the matrix is dissolved after deformation, by means of an acid not reacting with the fiber material, such as nitric acid.

As noted before, fiber bundles of the completed cable may follow a zigzag-, wave- and/or helix-shaped course, while, for example, several bundles may be made into a plait, a knit configuration, a web and/or a hose and/or a chord or a yarn. Such a configuration of fiber bundles may be implemented in a form-giving process subjecting the fibers substantially to bending only without any of the elongation and reduction in diameter performed in the process of producing the fibers from wires. In this form-giving process each fiber bundle may be subjected to being twisted together with the matrix before the matrix is dissolved or after matrix dissolution. Furthermore, it may be formed, in accordance with the desired type of the cable to be produced, as an individual bundle in zigzag-, wave- or helix-shape, and/or be connected with other fiber bundles.

If the twisting and/or plaiting and/or any other form giving performed on the fiber bundle is carried out before dissolving the matrix, then the connection between the fibers and the matrix will guarantee, that the fibers will become bent in the same manner the matrix that surrounds them is bent, without any fracture of the fibers. The ductility and/or the strength of the fibers may be further influenced in desired manner by heat treatment, such as by soft annealing or solution annealing and/or aging. This heat treatment may be carried out after the fibers have been made of wires, in a process preserving the volume, but involving elongation and reduction in cross-sectional area, specifically before and/or during and/or after dissolving the matrix, as well as before and/or during and/or after the form giving of the fibers taking place in the aforedescribed manner without any substantial elongation and reduction in cross-sectional area. If the fibers consist of a titanium-alloy of the beta-type and particularly if, in addition, a cold-forming step is included at least in the end phase of the multi-step deformation process used in the manufacture of the fibers by elongation and reduction in cross-sectional area, then the strength of the fibers may be additionally increased by means of heat treatment, such as solution annealing and/or aging. Furthermore, the fibers may be subjected to anodic oxidation immediately after having produced a bundle or only after the fiber bundle has been deformed into zigzag-, wave-, or helix-shape, and/or connected with other fiber bundles, but obviously after the matrix has been dissolved. For this purpose, a fiber bundle or a fiber configuration comprising several fiber bundles may be oxidized in an oxidizing electrolytic liquid, for example in diluted phosphoric acid, at voltages rising in the course of the process up to 50 volts or up to 100 volts.

BRIEF DESCRIPTION OF THE DRAWINGS

The subject matter of the invention will now be explained by making reference to the appended drawings illustrating several embodiments of the cable of the invention. There show.

DETAILED DESCRIPTION OF THE PREFERRED EMBODIMENTS

Figure 1:
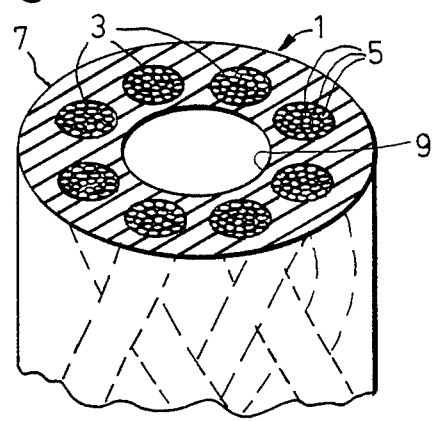
FIG. 1 a schematic oblique cross-section of a cable showing fiber bundles interwoven, to form a hose-shaped fiber configuration, FIG. 2 a schematic side view of a longer section of the fiber configuration of the cable shown in FIG. 1, the cable insulation being removed, FIG. 3 a schematic oblique cross-section of a cable comprising two groups of fiber bundles electrically insulated with respect to each other, FIG. 4 a schematic oblique cross-section of a cable comprising three fiber bundles electrically insulated with respect to each other, and FIG. 5 a schematic oblique cross-section of a cable comprising but one single bundle of fibers.

The hose-shaped cable 1 shown in FIG. 1 has a circular cross-section and comprises eight bundles (or less, if required), of substantially circular cross-sectional shapes, and a number of metallic fibers 5 per bundle, of circular cross-section. To be sure, only a fraction of the actual number of fibers is shown in FIG. 1. The fiber diameters and especially the distances between the fibers are shown greatly magnified in relation to the outer diameter of the cable. The bundles 3 are imbedded into an electrical insulation 7 of annular cross-section. The insulation 7 comprises a central longitudinal opening 9 of circular cross-section, and is effective to insulate the bundles 3 both with respect to the outside and with respect to the longitudinal opening 9. The insulation 7 consists of a rubberelastic material possessing good pliability (flexibility) and biocompatibility, such as an elastomer based on polyurethane or silicon.

Figure 2:
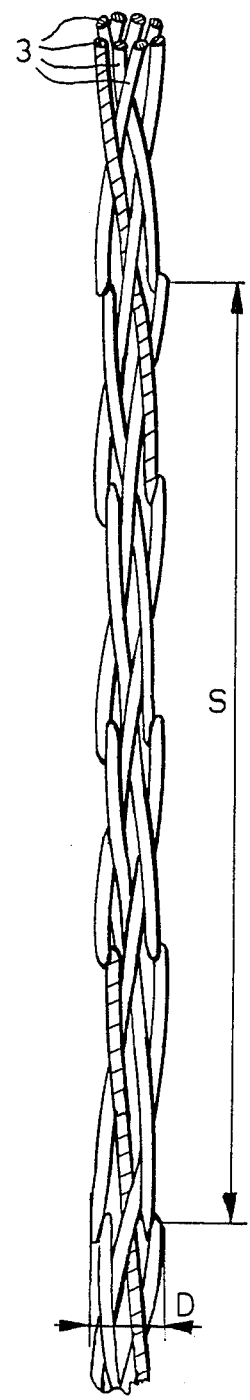

The eight bundles 3 with their fibers 5 are electrically connected in parallel, and constitute together the electrical conductor of the cable 1. The individual bundles 3 may be connected — in accordance with FIG.2 — to form an interconnected fiber . configuration, specifically a hose-shaped plait, in which one half of the bundles are wound in one direction of rotation, and the other half in the opposite direction of rotation around the longitudinal axis of the cable. The angle of plait, i.e. the angle formed by the bundles 3 — as well as by each of their fibers — with the longitudinal axis of the cable, should be not more than 50°, and preferably considerably less. One may assign to each of the bundles 3 twisted around the longitudinal axis of the cable a value of pitch S, in analogy to the pitch of a helix, this pitch S to be at least equal 5 times, preferably 10 times the outer diameter D of the hose-shaped plait formed by the bundles 3. To make the meaning and the dimension of the pitch S in FIG. 2 more clearly understandable, FIG. 2 shows one of the bundles 3 set off by means of shading. The insulation 7 not shown in FIG. 2 but readily visible in FIG. 1, encloses the bundles 3 at the outer perimeter of the cable 1. Therefore, the outer diameter of the cable 1 is somewhat larger than the diameter D visible in FIG. 2. However, it is to advantage to have the pitch S also equal to at least 5 times, and preferably 10 times the outer diameter of the cable 1. The fibers 5 of a bundle 3 may run parallel to the longitudinal axis of the bundle 3, or be twisted around said longitudinal axis. If the fibers 5 are twisted (snaked) in this way around each other,- then the pitch by which they are wound around the longitudinal axis of the bundle is to be equal 5 times and preferably 10 times the diameter D, at least,or even 5 times and preferably 10 times the outer diameter of the cable 1, at least.

The various bundles 3 are plaited to advantage in a comparatively loose manner, giving rise to clearance spaces between the adjacent bundles 3, at least in places. As may be concluded from FIG. 1, the insulation 7 can occupy the clearance spaces existing between the bundles 3, at least in places. However, adjacent bundles may also come in contact with each other, at least in places.

If the cable 1 gets curved or twisted while in use, the bundles 3 will be able to move with respect to each other. The plait will thus become easy to stretch, bend or twist, while any deformation will cause the rubberelastic insulation 7 to be deformed too.

A bundle 3 may comprise, for example, 100 fibers 5 having a circular cross-section, neglecting any deviations from the circular caused by surface roughness, and a diameter of about 12 to 13 micrometers. The total cross-sectional area of the fibres 5 of one bundle 3 has a value of 0.012 mm². An individual wire of the same cross-sectional area would have a diameter of 0.125 mm. Since the fibers 5 do not completely fill the cross-sectional area occupied by a bundle 3, it follows that the area of the bundle is somewhat larger than the cross-sectional area of the previously mentioned individual wire, and has a value of approximately 0.02 mm², corresponding to a bundle diameter of about 0.16 mm. This allows producing cables of a comparatively small diameter. Thus, the diameter D of the hose-shaped plait may be, for example, in the range between 0.6 and 1.5 mm. The outer diameter of the entire cable may then be a few tenths of a millimeter larger, depending upon the thickness of the insulation.

The fibers 5 may consist of a TiNb-alloy containing 40% by weight niobium and the rest titanium, the alloy having been, perhaps, subjected to heat treatment after the fibers have been produced by deformation. Such an alloy has a modulus of elasticity of 70 GPa and a fatigue stress of about 0.4 GPa. If these two values are inserted into the formula (2), there results a critical radius of curvature of only 0.9 mm. The TiNb-alloy has a breaking (ultimate tension) stress of about 0.8 GPa if subjected to a single tension load. A bundle 3 with 100 fibers 5 therefore has a tensile strength of about 10N. The tensile strength of a hose for example consisting of eight bundles interwoven with each other in accordance with FIG. 1, is equal approximately to the product of the number of bundles times the tensile strength of a bundle.

The TiNb-alloy has a specific electrical resistance of 86$\mu\Omega$cm. A bundle 3 comprising 100 fibers S running parallel to the longitudinal direction of the bundle and having the aforementioned diameter, has a resistance of 70$\Omega$per meter of length. If the plaiting angle, i.e. the angle between the longitudinal direction of the cable and the bundles has a value of 30°, then the length of a bundle 3 and of each fiber 5 will be equal to 1.16 times the length of the cable. The eight bundles of the cable connected electrically parallel with each other will then yield a resistance of approximately 10.1$\Omega$ per meter of cable length.

The number of fiber bundles belonging to a cable and plaited with each other may evidently be varied, and raised easily for example to 10. In this latter case, the ultimate tensile strength of the hose-shaped plait will become raised to about 100N, whereas the electrical resistance of the cable will become reduced to about 8.1$\Omega$per meter of length. Evidently the number of fibers per bundle may also be modified, for example raised. A bundle may easily contain for example about 200 or about 500 fibers, or even more fibers than that.

In a different embodiment of the cable of the invention, each fiber bundle shown in the FIGS. 1 and 2 contains 100 fibers of circular cross-section and of a diameter of 17 micrometers. The fibers 5 may consist, instead of the aforementioned TiNb-alloy, of an TiMoZrAl-alloy containing 15% by weight molybdenum, 5% by weight zirconium, 3% by weight aluminum, and the rest titanium, the alloy being subjected to aging after the fibers have been produced. This fiber material has a modulus of elasticity of 90 GPa and an allowable fatigue stress of about 0.7 Pa, so that formula (2) yields a critical radius of curvature of 1.2 mm. The fiber material has an ultimate tension stress, at single subjection to tension, of 1.2 GPa, so that a bundle of 100 fibers 5 will possess a tensile strength of about 30N The specific resistance of the TiMoZrAl-alloy has a value of 90 cm, yielding a resistance value for a fiber bundle of 35$\mu\Omega$per meter of length.

If the cable 1 is meant to serve as component of a cardiac pacemaker, there may be provided at the heart-end of the cable a contact electrode to act as an activator, effective to connect the conductor constituted by the totality of fibers 5 with the tissue to be stimulated. In this case the contact electrode is preferably provided with a closure adapted to seal the longitudinal opening 9 tight, for example with a sleeve enclosing the terminal section of the insulation 7 and being fastened thereto. At the other end, the cable may be provided with a connector, which in turn may be connected to an electrical pulse generator. The contact electrode and the connector may be fastened to the cable fixedly or looseably and may constitute together with the cable an electrical conducting device. In the implanted state of the cardiac pacemaker the cable 1 is effective to electrically connect the pulse generator with the contact electrode. In other respects, the cable 1 is constructed in a way to have a so-called stylet, implemented as a wire-shaped stud, or arranged to comprise such a stud, inserted into the longitudinal opening 9, from its end meant to be connected with the pulse generator. By the use of this stylet the end of the cable provided with the contact electrode may then be inserted through an artery into the heart of the patient. If the stylet is then pulled out of the longitudinal opening 9, the opening 9 may be closed off, if circumstances permit, even at the end of the cable 1 adapted to be connected with the pulse generator.

Figure 3:
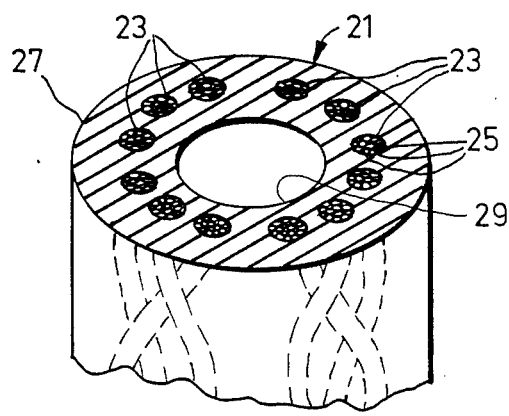

The twin cable 21 shown in FIG. 3 comprises two groups of bundles 23 imbedded in an insulation 27, each bundle 23 comprising a number of fibers 25, and the cable comprising in its inside a free longitudinal opening 29. The bundles 23 are plaited and adapted to constitute conductors electrically insulated with respect to each other, and serving as carriers of various electrical voltages. The two groups of bundles may each contain between 4 and 8, and for example according to FIG. 3, 6 bundles 23, each bundle containing 100 fibers or more. The two bundles 23 are arranged to run parallel to the longitudinal axis of the cable 21. The plaiting angle may lie around 30°, as is the case in the embodiment shown in FIGS. 1 and 2. Since, however, the bundles 23 are not fully wound around the longitudinal axis of the cable, they are actually not helix-shaped but rather zigzag- or wave-shaped, and may therefore contain, in places, such as at their peaks or wave crests, sections running more or less parallel to the longitudinal axis of the cable. As an alternative, instead of running parallel to the longitudinal axis of the cable, the two groups of cables may be wound, in their entirety, helically around the longitudinal axis of the cable. The two bundles 23 may be electrically connected with two separate contact electrodes, at one end of the cable 21, and with two separate connectors at its other end.

Figure 4:
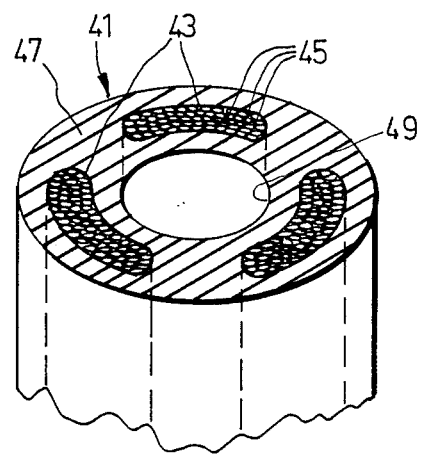

The triplet-cable 41 shown in FIG. 4 possesses three bundles 43 curved in cross-section and comprising the fibers 45 preferably slightly twisted or possibly parallel to the longitudinal direction of their bundle. The bundles 43 are imbedded into the jacket of a sleeve-shaped insulation 47 having an annular cross-section and are insulated against the outside, against the central longitudinal opening 49, and against each other. The bundles 43 run parallel to the longitudinal axis of the cable, they could, however, be wound around this axis. Since the cable 41 comprises three conductors electrically insulated against each other and consisting each of a single fiber bundle, the bundles comprise each, to advantage, 500 or more, or 1000 or more fibers.

Figure 5:
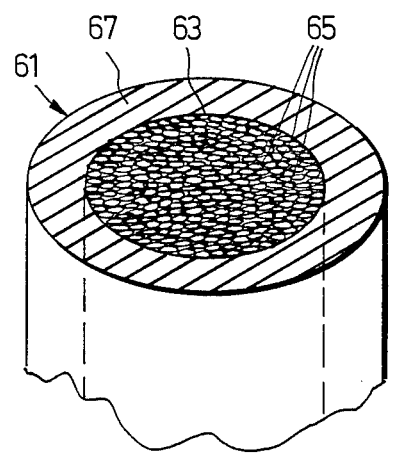

The cable 61 shown in FIG. 5 fills in cross-section a complete circle and comprises a centrally disposed electrical conductor consisting of a bundle 63 running parallel and coaxial to the longitudinal axis of the cable and having for example 500 or more, or 1000 or more fibers 65, which in turn are preferably twisted, i.e. wound around the longitudinal axis of the cable or possibly arranged to run parallel to said longitudinal axis. The conductor is enclosed inside an insulation 67 annular in cross-section and could consist, as an alternative, of several fiber bundles, rather than a single one, which would be wound around the longitudinal axis of the cable, i.e. twisted or plaited.

The metallic fibers of the cables shown in FIGS. 3, 4 and 5 may consist of one of the alloys specified in conjunction with the fibers 3, and may also have the same or similar cross-sectional dimensions as the fibers 3.

The fibers required for producing the cables shown in the various figures, may be manufactured in accordance with the manufacturing method described in the introduction and its variants. With this manufacturing method fiber bundles may be produced, for example, by deformation and dissolution of the matrix metal, in such a way that each bundle will contain exactly the number of fibers prescribed for a bundle of a cable. In this case, the fiber bundles may be plaited, to produce cables according to FIGS. 1 or 3, before dissolving the matrix by means of an acid. However, the fiber bundles may be made to contain each a number of fibers smaller or larger than the number specified for a bundle of a specific cable, such bundles could then be assembled in required numbers into one bundle specified for a particular cable, or they could be subdivided each into smaller bundles required for a specific cable.

The cables may be modified in other respects too. It would be possible to provide, for example, fiber bundles substantially elliptical or even rectangular in cross-section. It would be possible, furthermore, to allow several fiber bundles intended to yield together a conductor, to run around the longitudinal axis of the cable without plaiting, in the manner of a multiple thread, or parallel to the longitudinal axis of the cable. The cables illustrated in the FIGS. 4 and 5 could be modified to such an end, that each conductor be subdivided into several mutually plaited fiber bundles. Thus, in the fiber bundle of FIG. 5 the fibers, rather than being mutually plaited, could be twisted, i.e. wound around the longitudinal axis of the cable.

Furthermore, it would be possible to provide a cable comprising two conductors, each consisting of one or more fiber bundles, one of the conductors being arranged to enclose the other conductor, the two conductors being separated from each other in cross-section by an annular layer of insulation.

Instead of transiently inserting a stylet into the longitudinal opening of the cables provided with a central longitudinal opening, before introducing the cables into a human or animal body, it would be possible to equip the cables with a steel wire placed, in the course of their being manufactured, into the interior of the cable, to serve as a provisional stylet. In this case, when putting the cable to use, no additional stylet would be required, the provisional stylet would have to be removed after the cable has been introduced into the body.

Furthermore, the fibers would not necessarily have to be imbedded directly into the insulation, but it may be sufficient, circumstances permitting, to provide an insulating jacket enclosing the conductors on the outside, and perhaps an additional insulating coaxial hose disposed inside the conductors.

While there are shown and described present preferred embodiments of the invention, it is to be distinctly understood, that the invention is not limited thereto but may be otherwise variously embodied and practiced within the scope of the appended claims.

What is claimed is:

1. Electrical cable for performing stimulations and/or measurements inside a human or animal body, for instance for a cardiac pacemaker, the cable comprising at least one bundle of fibers, wherein each fiber is less than 20 micrometers thick and has a cross-sectional area of a single metallic material.

2. Cable as claimed in claim 1, wherein the fibers are substantially round in cross-section.

3. Cable as claimed in claim 1, wherein the fibers are not more than 15 micrometers thick.

4. Cable as claimed in claim 1, wherein the at least one bundle, comprises at least 100 fibers.

5. Cable as claimed in claim 1, wherein the at least one bundle, comprises at least 200 fibers.

6. Cable as claimed in claim 1, wherein the at least one bundle, comprises at least 100 fibers.

7. Cable as claimed in claim 1, wherein the fibers are arranged to run at least generally one of parallel and obliquely to the longitudinal direction of the cable so that each fiber is at most 50% longer than the cable itself.

8. Cable as claimed in claim 1, wherein the fibers are arranged to run at least generally one of parallel and obliquely to the longitudinal direction of the cable, so that each fiber is at most 30% longer than the cable itself.

9. Cable as claimed in claim 1, wherein the fibers are wound around the longitudinal axis of their bundle.

10. Cable as claimed in claim 1, wherein the at least one bundle of fibers, is arranged to run obliquely to the longitudinal direction of the cable, at least generally.

11. Cable as claimed in claim 1, wherein the at least one bundle of fibers, is implemented zigzag-shaped and/or wave-shaped and/or helix-shaped.

12. Cable as claimed in claim 1 comprising two or more bundles of fibers, wherein the bundles are plaited, knit, woven or twisted into a joined formation.

13. Cable as claimed in claim 1, wherein the fibers are arranged to run parallel to the longitudinal axis of their bundle, and/or the at least one bundle runs parallel to the longitudinal direction of the cable.

14. Cable as claimed in claim 1, wherein at least some of the adjacent fibers belonging to the same bundle are in contact with each other, at least in places.

15. Cable as claimed in claim 1, wherein the at least one bundle is insulated, at least on the outside, by a rubber-elastic insulation.

16. Cable as claimed in claim 1, wherein several bundles of fibers are imbedded into the annular jacket of a rubber-elastic insulation comprising a central opening extending in the longitudinal direction of the insulation.

17. Cable as claimed in claim 1, wherein at least two groups of fiber bundles are provided and electrically insulated from one another, each group comprising one or more fiber bundles.

18. Cable as claimed in claim 1, wherein the fibers comprise a metallic material consisting in part of titanium.

19. Cable as claimed in claim 18, wherein the titanium forms with at least one other metallic element an alloy of the beta-type.

20. Cable as claimed in claim 18, wherein the titanium comprises at least 50% by weight of the alloy.

21. Cable as claimed in claim 18, wherein the fibers also contain at least one metal of the group of metals including niobium, tantalum, zirconium, chromium, molybdenum, iron and aluminum.

22. Cable as claimed in claim 1, wherein the fibers are coated with a metal oxide coat.

23. Method of manufacturing an electrical cable for performing stimulations and/or measurements inside of a human or animal body, the cable comprising at least one bundle of fibers which are less than 20 micrometers thick, the method comprising the steps of: providing a number of wires thicker than the fibers and made of the same metallic material as the fibers to be produced; imbedding the thicker wires into a matrix consisting of a different metallic material; subjecting the thicker wires together with the matrix to a deformation process during which the wires are made longer and thinner; and, subsequently dissolving the matrix with an acid to yield a bundle of said fibers.

24. Method as claimed in claim 23, wherein the deformation subjecting step includes subjecting the fibers to cold-deformation and subsequently to heat treatment.

25. Method as claimed in claim 24, wherein the subjecting step includes subjecting the fibers to heat treatment comprising at least one of soft-annealing, solution-annealing and aging.

26. Method as claimed in claim 23, and further comprising the step of subjecting the fibers to anodic oxidation.

27. Cable as claimed in claim 1, wherein said metallic material is a titanium-niobium alloy of the beta-type.

28. Cable as claimed in claim 1, wherein each fiber and the at least one bundle is arranged so that the fibers run parallel to the longitudinal direction of the cable or form with the longitudinal direction an angle of not more than 30°.

29. Cable as claimed in claim 1, wherein each fiber and the at least one bundle is arranged so that the fibers run parallel to the longitudinal direction of the cable or form with the longitudinal direction an angle of not more than 20°.

30. Cable as claimed in claim 1, wherein each fiber includes a layer of oxide which acts as an electrical insulator when no significant compression force acts upon it, but loses its insulating effect under compression.

31. An electrical cable for performing stimulations and/or measurements inside a human or animal body, for instance for a cardiac pacemaker, the cable comprising at least one bundle of fibers, wherein each fiber has a thickness of at most 15 micrometers and has a cross-sectional area of a beta-type titanium alloy.

32. Cable as claimed in claim 31, wherein each fiber and the at least one bundle is arranged so that the fibers run parallel to the longitudinal direction of the cable or form with the longitudinal direction an angle of not more than 30°.

33. Cable as claimed in claim 31, wherein each fiber and the at least one bundle is arranged so that the fibers run parallel to the longitudinal direction of the cable or form with the longitudinal direction an angle of not more than 20°.

34. Cable as claimed in claim 31, wherein said alloy is a titanium-niobium alloy.

35. Cable as claimed in claim 31, wherein the fibers are arranged to run at least generally one of parallel and obliquely to the longitudinal direction of the cable so that each fiber is at most 50% longer than the cable itself.

36. Cable as claimed in claim 31, wherein the fibers are arranged to run at least generally one of parallel and obliquely to the longitudinal direction of the cable so that each fiber is at most 30% longer than the cable itself.

37. An electrical cable for performing stimulations and/or measurements inside a human or animal body, for instance for a cardiac pacemaker, the cable comprising at least one bundle of fibers, wherein each fiber is less than 20 micrometers thick and has a cross-sectional area of a beta-type titanium alloy, the fibers being arranged to run at least generally one of parallel and obliquely to the longitudinal direction of the cable so that each fiber is at most 30% longer than the cable itself.

* * * * *